US00PP11221P

United States Patent [19]

Zary

[11] Patent Number: Plant 11,221

[45] Date of Patent: Feb. 15, 2000

[54] FLORIBUNDA ROSE PLANT NAMED 'JACDRIVE'

[75] Inventor: Keith W. Zary, Thousand Oaks, Calif.

[73] Assignee: Bear Creek Gardens, Inc., Medford, Oreg.

[21] Appl. No.: 09/001,477

[22] Filed: Dec. 31, 1997

[51] Int. Cl.[7] ..... A01H 5/00

[52] U.S. Cl. ..... Plt./150

[58] Field of Search ..... Plt./150, 151, 139, Plt./140, 108

*Primary Examiner*—Howard J. Locker

*Attorney, Agent, or Firm*—Klarquist Sparkman Campbell Leigh & Whinston, LLP

[57] ABSTRACT

A floribunda rose plant having vigorous, upright, well-branched but compact growth; bright red flower color; cupped open flower form well filled with petals; leathery foliage; and high petal count.

1 Drawing Sheet

The present invention relates to a new and distinct variety of rose plant ot the floribunda class which was originated by me by crossing the variety 'AROcore', U.S. Plant Pat. No. 6813, with the variety 'Europeana', U.S. Plant Pat. No. 2540. The primary objective of this breeding was to produce a new rose variety having the large bright red flowers, high petal count and vigorous growth of the female parent combined with the compact, well-branched habit and dark green, leathery foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Bright red flower color;
2. Cupped open blooms well-filled with petals;
3. Vigorous, upright, well-branched growth that remains compact;
4. Leathery foliage;
5. High petal count. JACdrive has flowers that open into a cupped flower with the center remaining covered or nearly covered with petals. This gives an old-fashioned look to the flowers. Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using teminology in accordance with The Royal Horticultural Society (London) Colour Chart, except where ordinary dictionary significance of color is indicated.

Parentage:

*Seed parent.*—AROcore (U.S. Plant Pat. No. 6813).

*Pollen parent.*—Europeana (U.S. Plant Pat. No. 2,540).

Classification:

*Botanical.*—Rosa hybrida.

*Commercial.*—Floribunda.

FLOWER

Observations made from specimens grown in a garden environments at Somis, Calif. from January, 1996–August, 1997.

ksBlooming habit. Recurrent.

Bud:

*Size.*—One inch long when the petals start to unfurl.

*Form.*—The bud form is short, globular.

*Color.*—When sepals first divide, bud color is Red Group 46A. When half blown, the upper and lower sides of the petals are Red Group 45B.

*Sepals.*—Color: Green group 138B. Surface texture: Covered with many fine hairs. There are three normally appendaged sepals. There are two unappendaged sepals with hairy edges.

*Receptacle.*—Color: Green Group 137D. Shape: Funnel. Size: Medium (¼" long × 3/16" wide). Surface: Smooth.

*Peduncle.*—Length: Short (2½" to 3"). Surface: rough, prickly, glandular. Color: Medium green and bronzy. Strength: Stiff, erect.

Bloom:

*Size.*—Medium. Average open size is three inches.

*Borne.*—Several together in flat to slightly rounded clusters of three to five flowers.

*Stems.*—Short (10–14").

*Form.*—When first open: Globular. Permanence: Retains its form to the end, outer petals curl slightly.

*Petalage.*—Number of petals under normal conditions: 30–35.

*Color.*—The upper sides of the petals are Red Group 45B. The reverse sides of the petals are Red Group 45B. The base of each petal has a small (⅛" ×⅛"), whtishgreen half moon at the point of attachment. The major color on the upper side is Red Group 45B.

*Variegations.*—None.

*Discloration.*—At the end of the first day: No change. At the end of the third day: No change. By day six or seven there is a color change to Red-Purple Group 61B before petals begin to dry at day seven or eight.

*Fragrance.*—Slight.

Petals:

*Texture.*—Thick, leathery.

*Shape.*—Round.

*Form.*—Tips slightly recurved.

*Arrangement.*—Imbricated. Petaloids in the center are few.

*Persistance.*—Hang on and dry.

*Lastingness.*—On the plant: Long (seven days). As a cut flower: Not tested.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.
*Styles.*—Color: Reddish.
*Stigmas.*—Color: Greenish-white.

Plant:

*Form.*—Bush.
*Growth.*—Vigorous; upright; branching. After one full season of growth in Somis, Calif. is 3½' in height; and 2½' in width.
*Foliage.*—Number of leaflets on normal mid-stem leaves: Five or seven.
*Size.*—Medium (4½"×3–3½").
*Quantity.*—Abundant.
*Color.*—New foliage: Upper and Lower surfaces, Greyed-Red Group 178A. Old foliage: Upper surface: Green Group 136B. Lower surface: Green Group 139C.
*Shape.*—Pointed oval.
*Texture.*—Upper side: Leathery.
*Edge.*—Serrated.
*Serration.*—Single, small.
*Petiole rachis.*—Color: Reddish.
*Petiole underside.*—Smooth with occasional prickles.
*Stipules.*—Medium . (⅜–½" long); serrated, bearded.
*Disease resistance.*—Susceptible to mildew but resistant to rust under normal growing conditions at Somis, Calif.

Wood:

*New wood.*—Color: Reddish but quickly turns green. Bark: Smooth.
*Old wood.*—Color: Green. Bark: Smooth.

Prickles:

*Quantity.*—On main canes from base: Many. On laterals from main canes: Many.
*Form.*—Medium (¼"); hooked slightly downward.
*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by vigorous, upright, well-branched but compact growth; bright red flower color; cupped open flower form well filled with petals; leathery foliage; and high petal count.

* * * * *

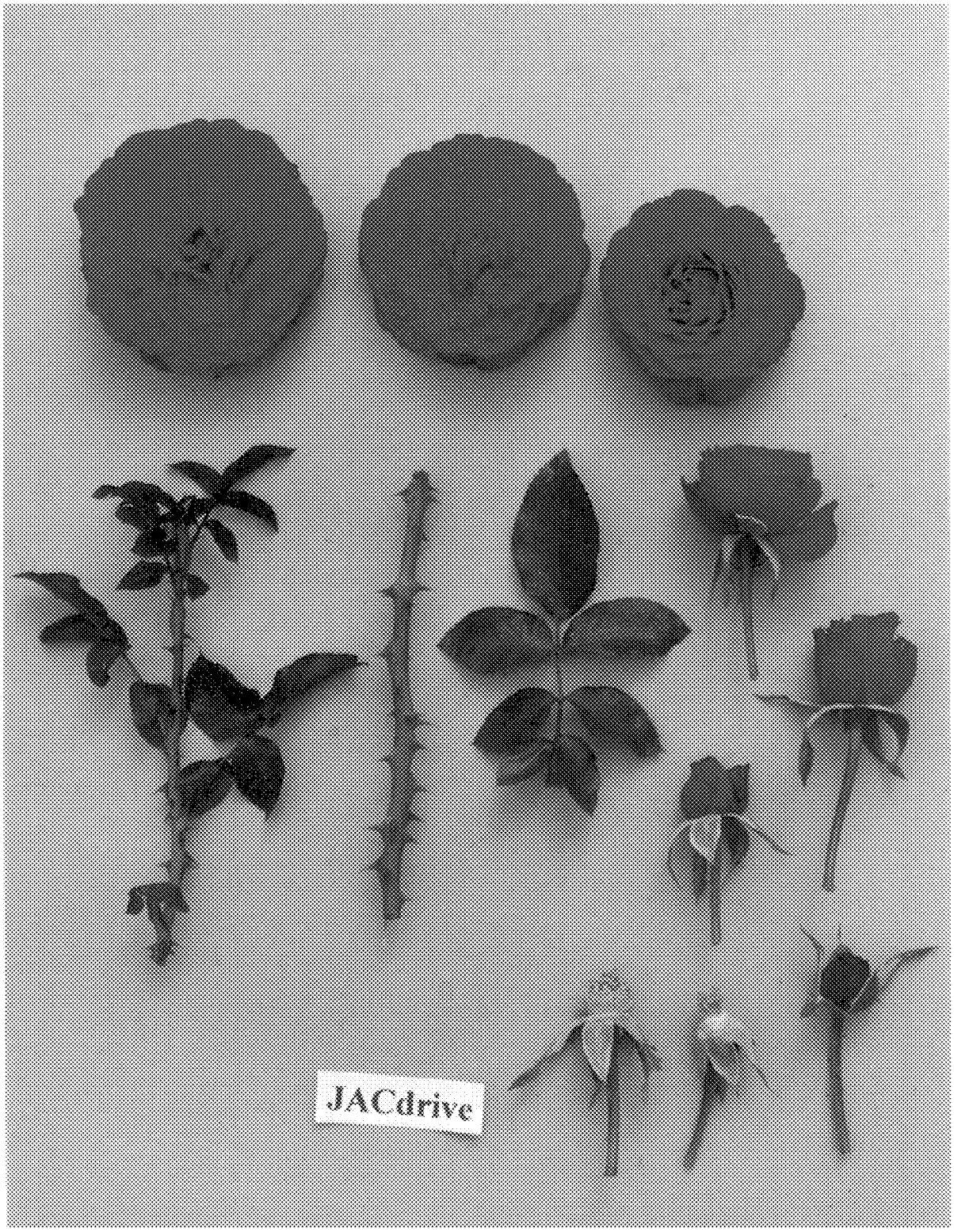
JACdrive

UNITED STATES PATENT AND TRADEMARK OFFICE

CERTIFICATE OF CORRECTION

PATENT NO. : PP 11,221
DATED : February 15, 2000
INVENTOR(S) : Keith W. Zary, Ph.D.

It is certified that error appears in the above-identified patent and that said Letters Patent is hereby corrected as shown below:

Specification:

Column 1,
Line 47, reads "environments", It should read -- environment --.
Line 49, reads "ksBlooming habit.". It should read -- Blooming habit: --.

Column 2,
Line 29, reads "whtishgreen". It should read -- whitish-green --.

Column 3,
Line 11, reads "Medium (4 1/2" x 3-3 1/2")". It should read -- Medium 4-4 1/2" x 3-3 1/2") --.
Line 23, reads "Medium. (3/8-1/2" long)". It should read -- Medium (3/8-1/2" long) --.

Signed and Sealed this

Eighteenth Day of September, 2001

*Attest:*

Nicholas P. Godici

*Attesting Officer*

NICHOLAS P. GODICI
*Acting Director of the United States Patent and Trademark Office*